United States Patent [19]

Froning

[11] 3,941,127
[45] Mar. 2, 1976

[54] APPARATUS AND METHOD FOR STEREOTAXIC LATERAL EXTRADURAL DISC PUNCTURE

[76] Inventor: Edward C. Froning, 215 N. San Mateo Drive, San Mateo, Calif. 94403

[22] Filed: Oct. 3, 1974

[21] Appl. No.: 511,655

[52] U.S. Cl. ............................. 128/215; 128/303 B
[51] Int. Cl.² ........................................... A61M 5/00
[58] Field of Search ............. 128/214, 214.2, 214.4, 128/215, 303 B, 329, 347, 2 B, 20, DIG. 26

[56] References Cited
OTHER PUBLICATIONS

Kendall–The Lamcet, Feb. 27, 1960, p. 474.
Ray–The Journal of Bone & Joint Surgery, pp. 760–761, Vol. 35-A, No. 3, July 1953.
Nadvornik et al.–Confin. Neurol. pp. 311–314, 34: 311–314, (1972).

Primary Examiner—Lawrence W. Trapp
Attorney, Agent, or Firm—Julian Caplan

[57] ABSTRACT

Apparatus consists of a stereotaxic fixture made up of a needle angle guide attached to an offset index, a parallel heading guide with plumb line chain attached, and a frame which provides fixation for the guides, allowing rapid and secure position readjustment, and which provides retention of orientation between the guides and the lumbar spine of the patient. The patient is positioned for the operation, preferably in full lateral (side lying) orientation of the spine, confirmed by the radiographic. image made preferably in posteroanterior projection. The midsaggital plane of the body is located at the skin surface by placing a first radiopaque marker corresponding to the center of the spine image. A second radiopaque skin marker is located at the side of the body of the patient for monitoring spine position while viewing profile radiographic image. The first marker provides a starting point from which to measure offset distance. The frame and heading guide are adjusted in position and secured in place, the heading guide radiographic image being superimposed on a line bisecting the angle between the adjacent vertebral end plates. The offset index is adjusted on the frame by means of the chain and its offset from the midsaggital plane (established from pre-operative radiograph) adjusted. A multiple needle technique puncture using the needle angle guide attached to the offset index to locate the site of skin puncture and the preferred 45° angle of penetration is utilized to allow gentle isolation of the nerve root crossing the disc in the target area of lateral approach, gentle enough to permit anesthesia under the semiconscious state of neuroleptanalgesia, supplemented by local anesthesia. Diagnostic and treatment drugs are injected in the nucleus pulposus through the lumen of the puncturing needle.

32 Claims, 16 Drawing Figures

APPARATUS AND METHOD FOR STEREOTAXIC LATERAL EXTRADURAL DISC PUNCTURE

This invention relates to a new and improved apparatus for stereotaxic lateral extradural lumbar disc puncture with features which protect the nerve root crossing over the surface of the disc in the target area of this approach.

More particularly, the invention has established utility in assisting the surgeon in locating needles for lateral disc puncture for accomplishing the operation of chemonucleolysis. In this operation, diagnostic radiographic contrast fluids are injected into the nucleus pulposus, as well as a fluid containing the enzyme chymopapain, which, when injected into the nucleus pulposus, decompresses, the disc, as discovered by Dr. Lyman Smith and set forth in U.S. Pat. No. 3,320,131.

A principal advantage of the invention is provision of means to pass the needle at approximately 45° off the midsaggital plane, which is an ideal approach since it is likely to clear the facet joint projection, on a heading parallel to the vertebral end plates outlining the disc space, sufficiently to gain direct access to the disc center and still clearing the projecting facet joint. The present invention provides apparatus which, when used with conventional radiographic equipment, assists the surgeon in the safe passage of needles for puncturing of the discs at an approach which is more likely to avoid contact with the nerve root crossing the target area of lateral extra-canal approach.

Further, the present invention provides a guidance system for all three planes of passage at an approach 45° off the midsaggital plane, providing depth control as well as a heading directly parallel to the vertebral end plates adjacent to each disc and directly over the prominence of the facet joint, presenting a suitable barrier to a medial passage of the needle which might enter the spinal canal and puncture the dural sac.

A feature of this invention is that use of the apparatus allows touching of the nerve root in a gentle enough manner to avoid injury to the nerve root during disc approach and, by permitting the patient to reveal the sensations of paresthesias produced by this nerve touching, to accurately guide the surgeon in maneuvering the docking needle around the nerve root, permitting isolation of the nerve root, and avoiding damage thereto during disc puncture.

Another feature of the invention is the provision of a guide, provided for the plural needle technique, and the plural needles, namely, a docking needle in which may be inserted a stylet to penetrate skin and muscle, then an obturator to isolate the nerve root crossing nearby and bring the lumen of the docking needle into direct contact with the disc at point blank range, which allows disc puncture by a fine caliber penetrating needle which is maintained on line by the wall of the docking needle, preventing bending of the fine caliber needle which occurs when such a fine caliber needle must be passed through the surrounding muscle by itself and unsupported. Preferably, the fine caliber needle is first used to inject a radiographically opaque contrast fluid into the nucleus pulposus of the disc for diagnosis by means of radiography. Where rupture of the disc is found, an enzyme such as chymopapain may be inserted for deflation of the remaining nucleus mucoproteins.

One of the features of the invention is the fact that the patient rests on his side on the operating table in a comfortable position. The position is also convenient from a surgeon's standpoint in adjusting the apparatus and inserting the needles.

Another feature of the invention is the saving of operation time. All of the needles may be placed before the rotation of the C-arm of the X-ray equipment to the horizontal projection may be necessary. Controlled depth of puncture utilizes triangulation to provide information in a third, posteroanterior plane, since the radiographic image only represents two planes when using one machine and such three-dimensional effect would otherwise have to be obtained by using two machines, one projecting 90° to the other. The second machine would have to be in the operating field, getting in the way of the arms of the operating surgeon.

Among the advantages of the method of the present invention are that nerve roots lying in the target of lateral extracanal approach are protected. Further, the patient preferably remains conscious during the operation and the surgeon may communicate with the patient to assist in guiding the docking needle and avoiding damage to the nerve root. Further, the docking needle serves as a sheath into which a plurality of other instruments may be installed, namely a stylet for puncturing the skin and muscle, an obturator for approaching the situs of the nerve root and avoiding piercing of the same and a puncturing needle for puncturing the disc and maneuvering the point of the puncturing needle within the disc for proper placement. A feature of this system is that the needles are kept out of the spinal canal and dura puncture is avoided.

Another feature of the present invention is that the depth of disc puncture may be accurately controlled, thereby preventing under or over puncture of the nucleus. The provision of a curve at the tip of the puncturing needle allows accurate maneuvering within the disc, as well as outside the disc, as is sometimes necessary when the docking needle itself cannot be easily maneuvered past the nerve. By using the hollow docking needle as a "well casing" for the curved puncturing needle, it is possible to direct the puncturing needle to the disc, a task which would otherwise be extremely difficult, in that the curvature of the needle would complicate immeasurably the maneuvering thereof.

Another feature of the invention is the control of the angle of lateral approach and adjustment to the actual depth of the disc from the skin surface as it varies from patient to patient and from one disc to the other in the same patient.

Another feature of the invention is that it provides visual sighting to a precise parallel heading with the disc vertebral borders as confirmed radiographic image.

Other objects of the present invention will become apparent upon reading the following specification and referring to the accompanying drawings in which similar characters of reference represent corresponding parts in each of the several views.

METHOD OF STEREOTAXIC LATERAL EXTRADURAL LUMBAR DISC PUNCTURE

Figure 1:
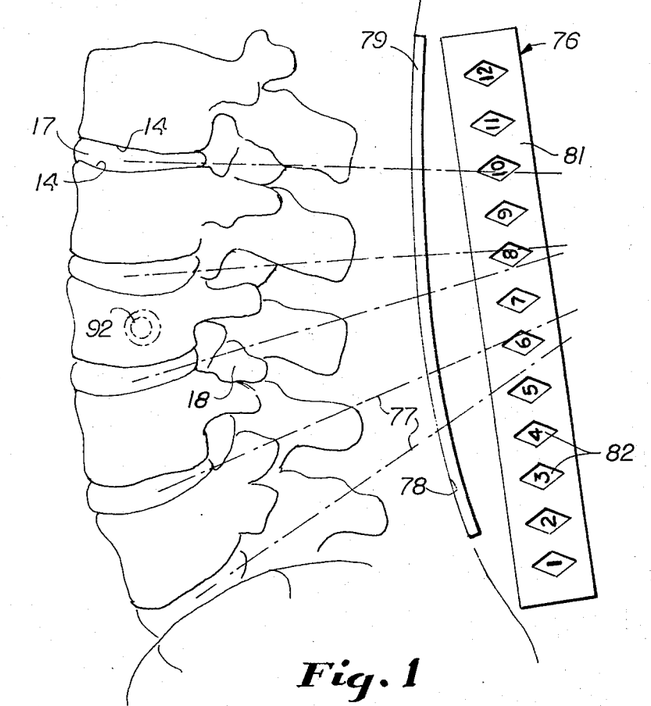
FIG. 1 is a schematic, top plan view of the lumbar vertebrae showing pre-operative markers used to determine distances and directions.
Figures 2, 3:
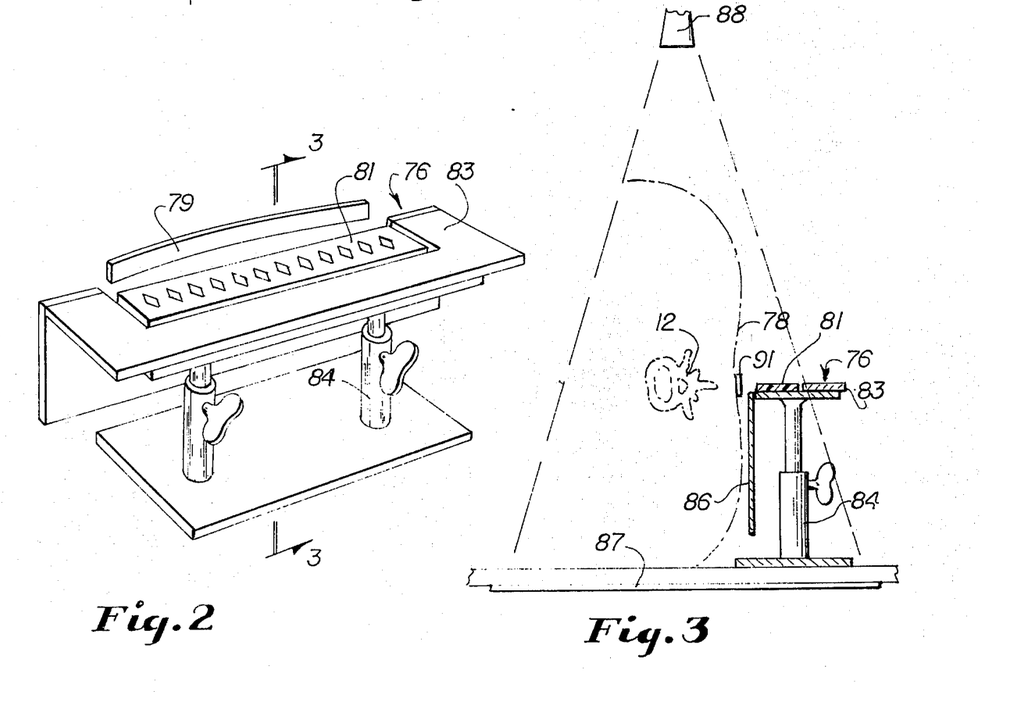
FIG. 2 is an enlarged perspective view of the marker and supporting stand.
FIG. 3 is a schematic vertical sectional view taken substantially along the line 3—3 of FIG. 2.

Pre-operative radiography is performed to determine the actual depth of the discs 17 chosen for puncture within the body of the individual patient and measurements made from a preliminary radiographic film 87 made in profile with the patient lying on his side with the most symptomatic side uppermost or the side with least surgical interference uppermost. A radiopaque interval marker reference 76 is positioned adjacent to the torso of the patient while making this film at such a distance from the film as to produce an equal magnification distortion between the markings 82 on this device and distances in the midsaggital plane of the patient's torso. One marker reference 76 comprises a ruler 81 having radiopaque numbers 82 therein mounted in a radiographic screen 83 supported by a stand 84. Scatter apron 86 depends from the patient-nearest edge of ruler 81. The apron 86 and screen 83 avoid burning or fogging the film and obscuring the images of the numbers 82 of the ruler 81 on the film 87 produced by the vertically positioned X-ray apparatus 88. The magnification distortion of the film image of the ruler 81 and of the vertebrae is proportionate in that the ruler is supported by stand 84 the same distance from film 87 as the vertebrae being filmed. Lines 77 are drawn on film 87 which bisect the angle between the vertical end plates 14 at each junction. A radiopaque strip 79 is attached upon the skin and held against the body with the same amount of pressure as the offset index 51 will be held during the operative procedure so that both will come to rest at the same distance from the center of the disc. The distance from the center of disc 17 to strip 79 as measured by the image of numbers 82 on film 87 represents disc depth below the skin.

The site of skin puncture for an angled needle approach at the preferred 45° at the midsaggital plane of the body is calculated to be equidistant to the depth of the disc center from the skin surface 78. Appropriate calculations for the offset skin puncture distance from the midsaggital plane can be calculated trigonometrically for variations from the 45° angle when such variations are advantageous. The 45° angle of approach, which begins on the skin surface 78 at a point equidistant to the depth of disc center from the skin surface allows an approach which clears the anterolateral prominence of the facet joint 18 (unless it is enlarged by anomalous formation or acquired change) and, at the same time, passes at an approach which allows this structure to prevent puncture of dura in the usual anatomical formation. This angle of approach, starting at a distance from the midline, calculated in this manner, is least likely to coincide with the location of the nerve root crossing the posterolateral surface of the disc, and most likely to make contact with the disc surface at a location relatively comfortable to the patient, lateral to the image of the pedicle 12 in the transverse plane of the body.

During performance of the operation, the patient is positioned as in the preoperative radiograph, preferably, lying on the side, upon a radiolucent table top, the most symptomatic side uppermost, or where osseous anomaly, or overgrowth, may present obstruction to the lateral approach to the disc, the side of least interference uppermost. The patient's torso is strapped, or retained, in a fashion so as to prevent drift out of lateral position, should this occur if the patient drifts off to sleep during the semiconscious anesthetic state preferable for this operation.

The skin is prepared by use of a routine disinfecting agent, a sterile plastic adherent sheet is placed over the skin, in the operative area. Heading guide supports 36, with the offset needle angle guide support 51 attached, (all hereinafter described) are fixed to the torso and to the adherent plastic sheet with commercially available adhesive strips so that the offset needle angle guide support 51 is positioned off the midline of the spine opposite to the side of needle approach and overlying the erector spinae muscles, as well as parallel to the spine. The offset needle angle guide support 51 is flexible so that is may conform to the curve of the low back surface.

Pain relief during the operation is provided by a combination of local anesthesia and neuroleptanalgesia, and where necessary, before the injection of chymopapain, for safety in the event of need for resuscitation against anaphylactic allergic shock, general anesthesia and tracheal intubation instituted after the disc puncturing needles are satisfactorily placed. The semi-conscious state makes possible a talk down with the patient over paraesthesias coming out of touch by the docking needle of the nerve root crossing the target area as the surgeon makes final maneuvers of approach to the posterolateral disc surface.

The optimum circumstances of the previously calculated 45° angle needle penetration approach necessitates an approach of the needle parallel to the vertebral end plates 14 of the disc junction as monitored by profile radiographic projection. This parallel heading usually coincides with the most prominent point on the curved surface of the facet joint 18. This mere precise heading can be expected to avoid arteries carrying significant circulation of the spinal canal.

The technique uses a plural needle (hereinafter described), an outer docking needle with an inner stylet, obturator and puncturing needle. The outer docking needle 56 is of large diameter, stiff enough to avoid bending by muscle; and an inner needle 59 of lesser caliber, well tolerated by the disc wall. The inner puncturing needle 59 has a beveled tip 67 and has a slight curve 66, placed near the tip, which allows change of direction off of the tip of the docking needle without the need to reposition the docking needle. This change of direction may be utilized to make fine maneuvers around the nerve root while the docking needle 56 is positioned to stand off from the disc surface, at point blank range, or it may be utilized to change directions within the substance of disc tissue while the outer needle 56 is held in a firm docking position with respect to the disc surface, and while it isolates the adjacent nerve root from potential damage by the puncturing needle. The outer docking needle 56 has an inside diameter sufficient to allow easy passage of the puncturing needle 59 within its lumen in spite of the curve placed in its tip, taking advantage of the elasticity of the needle material without exceeding its yield point. The needle hub 61 of the puncturing needle limits distance of passage of the lumen of the outer needle by the abutment of the hub 61 of one needle against the hub 56 of the other, thus limiting projection of the tip 67 of the puncturing needle beyond the tip of the docking needle as the diameter of the latter holds the depth of its passage at its resting position on the disc surface. This provides control of depth of disc puncture, thus confining the tip of the puncturing needle within the nucleus pulposus when it is directed towards disc center, preventing underpuncture or overpuncture of the nucleus pulposus to a position where the tip would lie within the substance of the annulus fibrosis. This optimum distance of projection of the tip 67 of the inner needle beyond the tip of the outer needle 56 is approximately 26 mm. for all or almost all adult subjects. The curve 66 in the tip of the puncturing needle is placed in the same direction as the bevel 67 since the bevel itself tends to cause change of direction of a needle as it passes through tissue.

In order to coordinate the three determinations of: (1) angle of approach of the docking needle 56, (2) depth of puncture of the various needles, and (3) a parallel heading with a profile view of the disc space, a stereotaxic fixture (hereinafter described in detail), is utilized. This device is a framework which is attached to the patient's torso and which allows fixation of the offset index-needle angle guide 57 and the parallel heading guide 46 in such a way as to make reposition of these two structures rapid, simple and secure.

Radiopaque markers 91 are placed on the skin surface 78 over the spinous processes 11, so that their images project over the midline of the spine in posteroanterior (or anteroposterior) radiographic projection. A similar radiopaque marker 92 is placed over the lateral surface of the body so that its image projects over a portion of the lumbar vertebral bones, preferably the body of the L4 vertebrae and on other vertebrae. These skin radiopaque markers 91, 92 are positioned after the patient's body is adjusted in posteroanterior radiographic projection to a fully lateral orientation, i.e., when the image of the spinous processes 11 projects midway between the image of the vertebral pedicles 12 while the radiographic tube 88 and screen (camera) are in a horizontal relationship. The radiographic skin markers 91 over the spinous processes identify the midsaggital plane to be used as a starting point for measuring skin puncture offset distance from the midline. The skin marker 92 on the lateral surface of the body acts as a means of recognizing drift of the patient's body off true lateral while radiographic monitoring is being viewed in profile projection.

The parallel heading guide 46 adjustably attached to the fixture is fashioned of a narrow thin piece of radiopaque material presenting less radiopacity than the docking needle 56, so as to allow visualization of the end of the docking needle when the two structures are superimposed in radiographic image. The position of the parallel heading guide 56 is adjusted until its radiographic image superimposes the disc space between the vertebral end plates 14, and is parallel to an ideal line or a line 77 bisecting the angle between them so as to reproduce, on a monitoring screen, the angle of the line drawn on the preoperative radiographic film 87. The radiographic tube and screen (camera) are positioned in full vertical relationship for alignment of the parallel heading guide 56 so as to coincide with the plumb line 48 next described, and the visual vertical orientation used by the surgeon while passing the needle.

A small chain 48 or other plumb device is attached to the tip of the parellel heading guide 46 for use as a plumb line. The parallel heading guide 46 is moved to a point where the tip of this chain 48 hangs directly upon the skin surface at the appropriate distance from the midline, identifying a skin puncture site which will be on line with a parallel heading to the disc space. The tip of this chain 48 is then lined up with the offset index-needle angle guide 51, placed at the appropriate distance offset from the midline. The point at which these two elements meet completes the perfect skin puncture site for each disc.

The skin puncture site is anesthetized with local anesthesia. The muscle is also infiltrated with local anesthesia. The needle used for this purpose is passed in the trough of the needle angle guide and its position is monitored radiographically providing further confirmation of the heading chosen for the disc intended for puncture.

The midline offset distance is coordinated with the depth of passage of the docking needle 56 in a direct interrelationship. The distance of the docking needle still available above the skin surface, after docking with the disc surface, is utilized for this relationship for practical application. Preferably a sleeve 62 placed over the docking needle 56 of an appropriate length to touch the skin surface when the docking needle can be expected to touch the disc surface. The length of the sleeve 62 is correlated with the midline offset distance. Sleeves 53 are provided for placement over the shaft 52 of the offset index-needle angle guide. These sleeves are color coded (and number coded) to coordinate with the various disc center depths encountered.

The half channel 54 of the needle angle guide 51 is preferably 26 mm. in length. This approximates the distance between the disc surface and the point at which the docking needle will ordinarily encounter the facet joint. The docking needle with stylet 56 inserted so as to conveniently penetrate muscle and muscle fascia is inserted at the puncture site preferably at an angle of 45° and parallel to the heading guide 46. The appropriate sleeve 62 on the docking needle will reach the edge of the needle angle guide 54 when the tip of the docking needle can be expected to approach the facet joint. At this point, the needle angle guide 57 can be moved out of position while the docking needle is advanced, in a direction established by passage through most of the muscle it will encounter to the disc surface. At this point, an obturator 63 with rounded tip is placed within the docking needle 56 in exchange for the stylet 58 with tapered point used to make penetration of the skin and muscle. As the sleeve 62 on the docking needle approaches the skin surface, the surgeon is aware that the tip of the obturator 63 in the docking needle is approaching the nerve root crossing the target area. At this point, the surgeon begins a talk down with the patient's symptoms. The location of symptoms in the lower extremity identifies paraesthesias. When the disc surface is sensitive (as is often the case when the herniation is located at or near the site of docking), local anesthesia may be injected through the docking needle over the disc surface. The surgeon holds the docking needle 56 directly on the disc surface so as to continuously isolate the adjacent nerve root while he inserts the curved puncturing needle 59 into the disc. The surgeon rotates the puncturing needle, when necessary, to change direction of passage of the puncturing needle within the disc substance, directing the curve 66 toward the change of direction desired. Particularly when syndesmophytes obstruct passage, this capacity allows passage to a central location even when bone permits such passage only be executing an "S" path of progress.

The lumbosacral joint is positioned so deep within the pelvis, in some patients, that iliac bone 16 presents an obstruction to a direct parallel heading with the lumbosacral disc. When this occurs, a more cephalad position of the skin puncture site is necessary. The curve 66 placed in the tip of the disc puncturing needle is particularly useful in this situation as it allows turning the corner with disc puncture after the docking needle is successfully placed at the edge of the disc surface. By turning this corner, the tip 67 of the disc puncturing needle can still be directed to the central portion of the nucleus pulposus. When a facet joint is enlarged by anomalous formation, or by acquired deformation, it may be far enough lateral so as to obstruct passage at a 45° angle by the appropriately calculated distance offset from the middle. In this situation, a slightly more lateral skin puncture site may then be utilized with the first positioned docking needle still in place, its tip still resting on the obstructing joint. The first placed docking needle provides a reference point for maneuver of this second placed docking needle so as to skirt the anterolateral surface of the obstructing joint.

After successful centering of the puncturing needles in the nucleus pulposus, the offset index-needle angle guide 51, and the parallel heading guide 46, are maneuvered successively to provide guidance for the next disc planned for puncture.

Pharmaceuticals are injected through the puncturing needle 59 into the nucleus pulposus by methods such as disclosed in Smith U.S. Pat. 3,320,131 for diagnosis and treatment.

ANATOMICAL CONSIDERATIONS AND PREOPERATIVE PROCEDURE

Preliminary to description of the apparatus, a description of certain details of the anatomy of the lumbar vertebrae is desirable. Each such vertebrae has a spinous process 11 which projects centrally of the spine and with the patient resting on the side projects generally horizontally toward the surgeon. To either side of the spinous process 11 (in a radiograph) are pedicles 12 which are quite readily apparent in a radiological view and in the position of the patient are vertically one above the other when viewed in side elevation and are vertically aligned when viewed in top plan. The discs 17 are somewhat obscured in the top plan but the dorsal profile laminar eminence 13 is readily apparent, and this casts a V-shaped laminar shadow. The dorsal prominence of this V coincides with the center of the facet joint of the disc 17 and hence helps in docking the needle precisely lateral to the position of the pedicle 12. In docking the end plates 14 of the vertebrae adjacent to the disc to be diagnosed and treated are used as locating means in both horizontal and vertical radiographic projection.

Iliac bone 16, particularly the iliac crest and the iliac wing constitute blockage to a vertical heading to the 5th disc possible at the superincumbent levels of L4 and above. The iliac bone does not usually present a blockage, however, when the heading is made parallel to the vertebral end plates outlining the 5th (lumbosacral) disc, with certain exceptions in individuals where the lumbosacral joint is positioned anatomically deeper in the pelvis than usual. Thus, the parallel heading guide provides a particular advantage in starting the needle on the skin surface at a point where the heading of the docking needle will clear the iliac crest.

Figure 4:
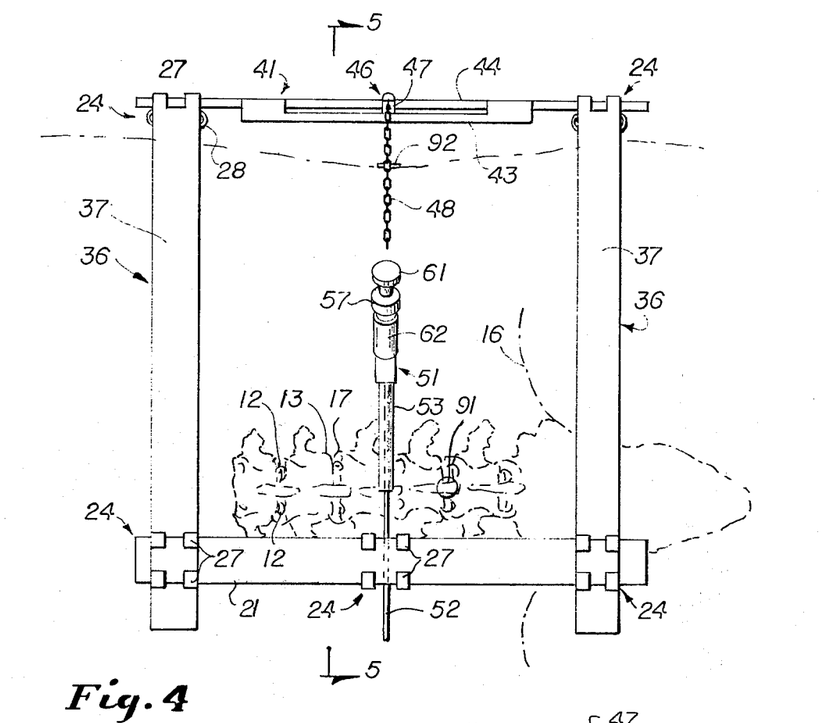
FIG. 4 is a side elevational view of one form of the apparatus showing the vertebrae schematically.

DESCRIPTION OF FIG. 4 MODIFICATION

Figures 5, 6:
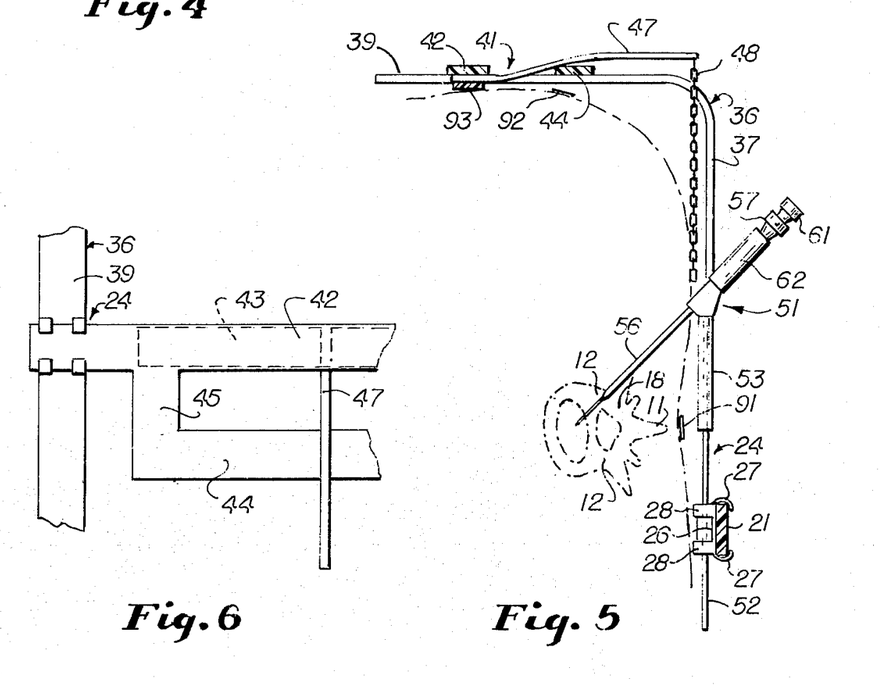
FIG. 5 is a sectional view taken substantially along the line 5—5 of FIG. 4.
FIG. 6 is a fragmentary top plan.
Figures 7, 8, 9:
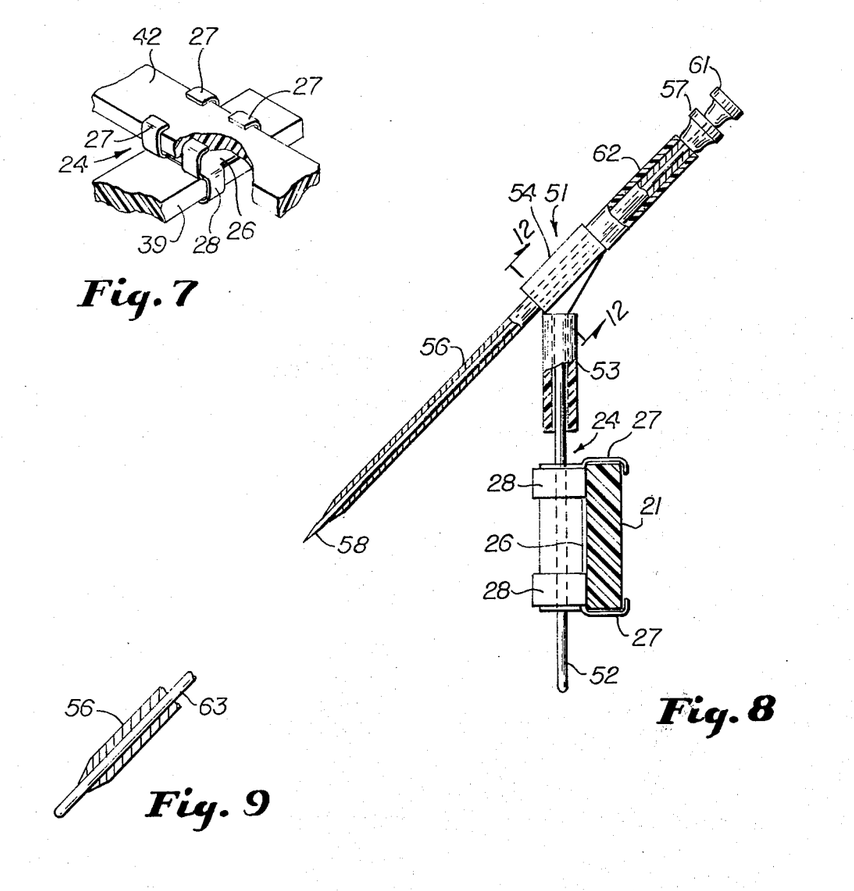
FIG. 7 is an enlarged, fragmentary perspective view of a portion of the apparatus partly broken away to show internal construction.
FIG. 8 is an enlarged fragmentary sectional view of a portion of the device taken substantially along the line 5—5 of FIG. 4.
FIG. 9 is a fragmentary sectional view of a modified needle construction.
Figure 10:
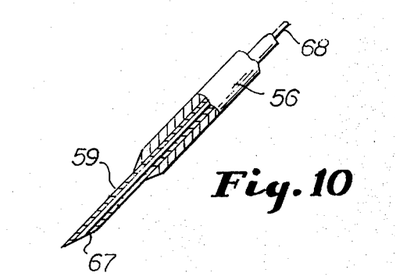
FIG. 10 is a fragmentary sectional view of still another modified needle construction.

Adjacent either end of horizontal index 21 positioned below but parallel to a line on the skin coinciding with the spinous processes 11 determined by markers 91, is a double clip 24. As shown in FIG. 7, said clip 24 has a body 26 preferably formed of sheet metal having at each corner forward bent fingers 27 which fit around the edges and over one face of index 21 and lateral fingers 28 which are bent around a member 36 of a cross section similar to the cross section of index 21. Heading guide supports 36 extend adjacent each end of index 21 vertically up along the back of the patient. Support 36 has a vertical arm 37 and at its upper end has a horizontal arm 39. Preferably arms 39 are level with each other. As is apparent from FIGS. 4 and 5, clips 24 may be moved inward and outward relative to index 21 and vertical arms 37 may also be moved upward and downward relative to clips 24 so that the horizontal arms 39 are in proper position. Arms 37 are then strapped to the patient by tape or other suitable means.

Supported by horizontal arms 39 is a longitudinally extending horizontal head guide longitudinal member 41. In the form best shown in FIG. 6 said member 41 is formed with a top strip 42 which is attached by means of a clip 24 to a horizontal arm 39 at either end. Below strip 42 for at least a portion of its length is bottom strip 43 which is spaced slightly from strip 42 for a purpose which hereinafter appears. Spaced horizontally forwardly from strip 42 is forward strip 44 connected to strip 42 by legs 45.

Member 41 supports a heading guide 46. In the form shown in FIG. 4, guide 46 comprises a thin, narrow, semi-radiologically opaque spring metal 47 and a depending chain 48. The proximal end of spring 47 is inserted between strips 42 and 43 and bent over the top of strip 44. Thus the spring 47 may be moved longitudinally and also adjusted in angular position on a heading bisecting the angle between the plates 14 of the adjacent vertebrae but is held in adjusted position by friction. The chain 48 hangs by gravity and serves as a locating guide for the needle guide 51 hereinafter described. By X-ray technique, the guide 46 is moved longitudinally of member 41 so that the chain 48 is positioned in alignment with each of the discs to be treated, it being understood that the guide 46 is moved serially from one disc to another as the operation proceeds.

Figures 13, 14:
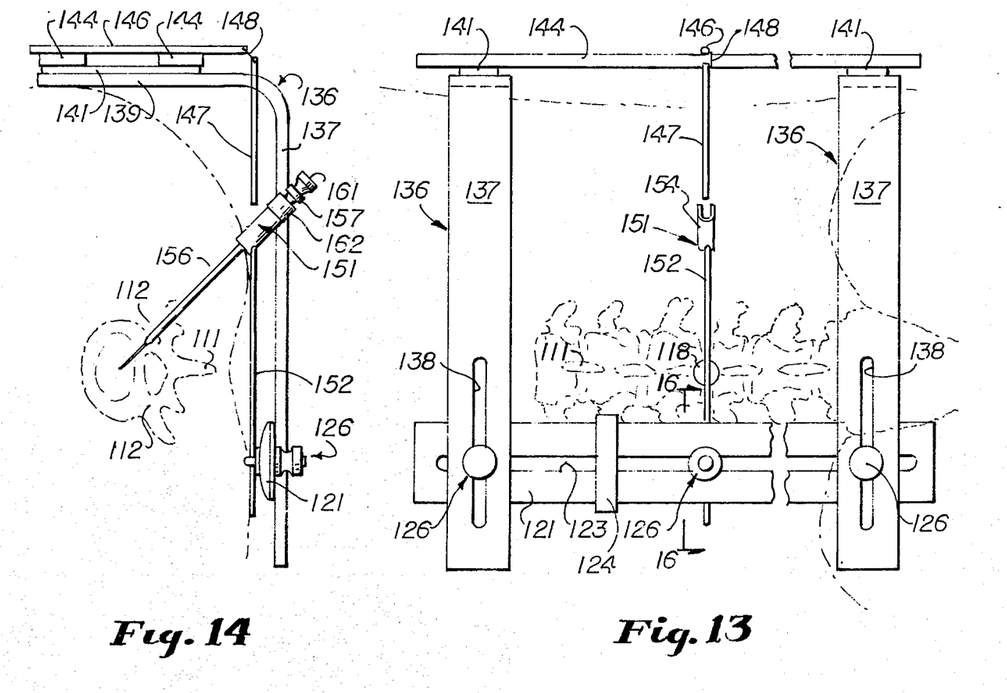
FIG. 13 is a view similar to FIG. 4 of a modification.
FIG. 14 is a view similar to FIG. 5 of the modification of FIG. 13.
Figures 15, 16:
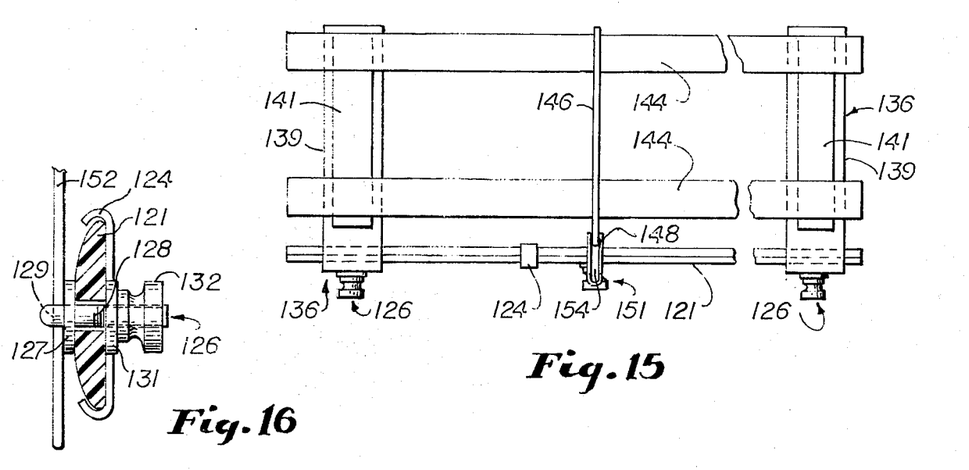
FIG. 15 is a top plan view partly broken away in section of a portion of the structure of FIG. 13.
FIG. 16 is an enlarged fragmentary sectional view taken substantially along the line 16—16 of FIG. 13.

Alternatively, a heading guide and magnetic means to attach it to heading member and magnetic means to attach the latter to arms 39 all as shown in FIGS. 13 to 15 may be substituted. Other attachment means may be used as will occur to one skilled in the art benefited by this specification. Similarly, vertical arm 37 may be attached to index 21 by the means shown in FIGS. 13–15 and other attachment means will occur to those skilled in the art.

Offset index-needle angle guide 51 has half round channel 54 from which depends needle guide arm 52. The angle between the channel in guide 51 and arm 52 is preferably 45° for the purpose heretofore mentioned. The lower end of arm 52 is secured by intermediate clip 24 which is slidable on index 21. Thus the clip 24 slides along index 21 until the guide 51 is immediately under the chain 48. By calculations made prior to the operation, it is determined the distance which channel 54 must be positioned above spinous process 11. This distance is equal to the depth of the center of disc 17 below the skin surface as per pre-operative radiograph. Once this determination has been made, a positioning sleeve 53 of proper length is slipped over the arm 52 and the channel 54 is brought down so that the lower end of sleeve 53 rests opposite the midline radiographically opaque markers 91. Preferably, the sleeves 53 are color coded or otherwise identifiable for different distances, the distances having been previously computed.

Figure 11:
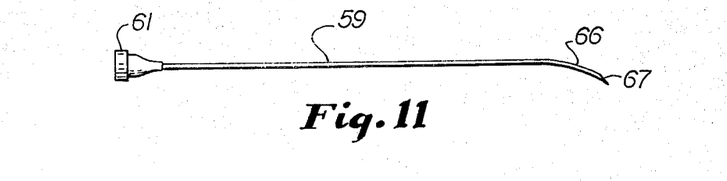
FIG. 11 is a fragmentary plan view of a portion of the needle of FIG. 10.
Figure 12:
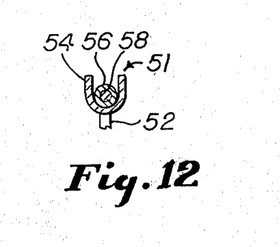
FIG. 12 is a sectional view taken substantially along the line 12—12 of FIG. 8.

A series of needles is slipped through the channel 54 in body 51. Preferably a docking needle 56 which is tubular and is formed at its outer end with a hub 57 is first used. Preliminary to insertion, as is shown in FIG. 8, a stylet 58 is inserted in the needle 56 so that its tip projects slightly to penetrate skin and muscle. For accurate determination of the maximum penetration, the preliminary radiological analysis has been made of the maximum distance which the tip of stylet 58 may penetrate to make contact with the disc to be treated but which will not be greater than said distance so that the stylet 58 or the puncturing needle 59 which is subsequently inserted will not injure the patient. For such purpose, a second penetrating control sleeve 62 similar in structure and function to sleeve 53 is installed over the docking needle 56 in contact with hub 57. For a 45° angle approach, sleeve 62 has a length relationship equal to 1.414 times of sleeve 53. Stylet 58 is then replaced by obturator 63 and the tip is brought into docking position as has been described in the discussion of the Method. After the docking needle 56 has been accurately positioned, the obturator 63 is withdrawn and a puncturing needle 59 replaces the stylet 58. This structure is shown in FIG. 11. Needle 59 has a curve 66 at its distal end terminating in a bevel 67. Initially a penetrating needle stylet 68 is installed to block the canal in the needle 59 to fill out the bevelled surface and make it smooth and to make the needle stronger.

Heading guide 46 is preferably of a material which is semi-radially opaque or half radiopaque and half radiolucent. Thus the guide 46 shows in the radiological view but does not obscure the needle 56 while docking against the disc while assisting the surgeon maneuver the docking needle into place.

With the puncturing needle 59 in place, a radiologically opaque fluid is inserted into the nucleus propulsus. Diagnosis of whether there is rupture or herniation of the disc is made radiologically. If rupture or herniation are apparent, the enzyme is inserted through the same puncturing needle 59.

All the needles can often be placed and adjusted to disc center before it is necessary to rotate the C arm of the mobile image intensifier to horizontal PA projection. This allows prompt placement of all needles using only one radiographic unit.

FIG. 13 MODIFICATION

In FIG. 13, guide 121 is offset below the spinous processes 111. In FIG. 13, the patient is adjusted so that processes 121 project in the midline halfway between the radiological shadows of the right and left pedicles 112.

For adjustment of fasteners 126 along the length of offset guide 121, a central slot 123 or several slots aligned end to end are formed in guide 121. To prevent the guide 121 from being distorted by a widening of the slot 123 under stress, a clip 124 may be used to hold the sides of the guide 121 a fixed distance apart, and preferably said clip is movable longitudinally of the guide so that it may be positioned in a location where it is not an obstruction to maneuver of the offset index needle angle guide.

At least three fasteners 126 are installed in slot 123, one at each end and one movable to a position opposite the disc being treated. Each fastener 126 has a non-circular base 127 which is positioned transversely of slot 123 and from which extends a shank 128 through the slot 123, the outer end of the shank 128 being threaded. An axially elongated slot 129 is formed in shank 128 or at least in the fastener 126 which is used at the middle of the guide. A washer 131 fits over shank 128 and nut 132 is threaded on to the end of the shank 128 to clamp the parts hereinafter described relative to guide 121.

At either end of guide 121 is installed a heading guide support 136 positioned to accommodate the shape of the patient. Each support 136 is L-shaped in end elevation. The vertical arm 137 is formed with an elongated slot 138 to receive shank 128. Fastener 126 thus secures support 136 in position longitudinally relative to offset guide 121 and also vertically so that the horizontal arm 139 of the support 136 overlies the patient. Preferably a metallic insert 141 is located in horizontal arm 139.

As has been stated, there are two heading guide supports 136, one at each end of the offset guide 121 and preferably these are adjusted in elevation so that they are level in a horizontal sense. A pair of heading guide strips 144 which are preferably of a magnetic material and thus magnetically adhere to inserts 141 bridge the space between the supports 136 and viewed in plan are respectively anterior and posterior to the vertebral body.

Heading guide 146 extends transversely across strips 144 and adheres thereto by reason of its metallic nature. The guide 146 is adjusted longitudinally and angularly so as to project over the interbody space parallel to the vertebral end plates 114 of the vertebrae adjacent to the disc being treated. Guide 146 is preferably of a material which is similar to heading guide 46 of the preceding modification for a similar function. Visual connecting rod 147 or a chain is connected to the outer end of guide 146 by means of an articulated joint 148 so that the force of gravity causes the rod 147 to extend vertically-downwardly to a position adjacent to guide 121.

Needle angle guide 151 is semi-tubular and connected to the upper end of needle guide offset index 152, preferably at an angle of 45°. Arm 152 projects through aperture 129 in the middle fastener 126. When adjusted in position, tightening of nut 132 causes the washer 131 to hold the arm 152 exactly vertical and the guide 151 at an angle of 45° to the saggital plane. The distance of projection of the arm 152 is predetermined from pre-operative trigonometric studies of the body relationship.

The needles used are similar to those of the preceding modification and the surgical procedures in their usage are similar. Several of the elements of the structure of FIG. 13 are similar to the preceding modification and the same reference numerals increased by 100 are used to designate corresponding parts. Various alternative means may be used to attach member 137 to index 121, or member 144 to member 139, or member 146 to member 144 or member 152 to index 121.

What is claimed is:

1. Apparatus for lateral extradural disc puncture comprising a frame for fixation to a patient,
an offset index,
a needle angle guide connected to said offset index at a predetermined angle,
first means adjustably positioning said offset index relative to said frame to determine the position of said needle angle guide both from the midsaggital plane of the patient and longitudinally relative to the intervertebral discs of said patient,
a heading guide,
second means adjustably positioning said heading guide relative to said frame longitudinally relative to said patient,
and plumb line establishing means on said heading guide positioned to hang down the back of the patient into proximity to said needle angle guide.

2. Apparatus according to claim 1 in which said frame comprises a horizontal index guide positioned along the back of the patient parallel to and below the spinous processes,
at least one heading guide support having a first stretch and a second stretch angularly related to said first stretch,
cooperating third means on said index guide and said first stretch for adjustably positioning said heading guide support vertically and horizontally relative to said index guide so that said second stretch overlies the patient,
and cooperating fourth means attaching said heading guide to said second stretch substantially horizontally,
said first means attached to said index guide,
said second means attached to said heading guide support.

3. Apparatus according to claim 2 in which there are at least two said heading guide supports parallel to each other and horizontally spaced from each other and two said third means, said heading guide supports being positioned adjacent opposite ends of said index guide.

4. Apparatus according to claim 3 in which said second means comprises plural heading guide strips and said heading guide is frictionally held between said plural heading guide strips.

5. Apparatus according to claim 4 in which there are two parallel, horizontally spaced apart heading guide strips, said strips attached by said fourth means to said second stretches of both said heading guide supports.

6. Apparatus according to claim 2 in which said heading guide support is formed as an L in end elevation.

7. Apparatus according to claim 2 in which said third means comprises a clip having a body between said index guide and said first stretch and a first set of fingers slidably engaging said index guide and a second set of fingers slidably engaging said first stretch.

8. Apparatus according to claim 2 in which said heading guide comprises a narrow semi-radiopaque member engaging said heading guide support and a flexible member depending from said last-named member and hanging therefrom by gravity.

9. Apparatus according to claim 8 in which said flexible member is semi radiologically opaque or partially radiologically opaque and partially radiologically lucent.

10. Apparatus according to claim 1 in which the angle between said needle angle guide and said offset index is 45°.

11. Apparatus according to claim 1 which further comprises a needle in said needle angle guide projectable relative to said needle angle guide to contact a vertebral disc at an angle of about 45° to the saggital plane of said disc.

12. Apparatus according to claim 11 in which said needle comprises a hollow lumen.

13. Apparatus according to claim 12 which further comprises a blunt stylet reciprocable within said lumen.

14. Apparatus according to claim 12 which further comprises a fine caliber hollow needle reciprocable within said lumen and suitable for injection into the disc of radiologically contrast fluid or a substance suitable for chemonucleolysis.

15. Apparatus according to claim 14 in which the distal end of said fine caliber needle is curved.

16. Apparatus according to claim 1 in which said offset index comprises an arm, a removable sleeve on said arm between said needle guide and said midsaggital plane indicating the distance of said needle guide from said plane.

17. Apparatus according to claim 1 which further comprises a needle through said needle angle guide, said needle having a hub and a removable sleeve on said needle between said hub and said needle angle guide indicating the penetration of said needle into the patient.

18. Apparatus according to claim 2 in which said index guide is formed with an elongated longitudinal first slot and said first stretch with a second elongated slot and said third means comprises a threaded member fitting through both said slots and having a head at one end and a nut on said threaded member.

19. Apparatus according to claim 2 in which said heading guide support is formed as a right angle in end elevation, said first stretch being vertical and formed with an elongated longitudinal slot, said second stretch being horizontal and overlying the patient, said second stretch being in at least a portion of its length magnetizable.

20. Apparatus according to claim 19 in which said heading guide support is of magnetic material and said fourth means comprises magnetic attraction of said heading guide support to said second stretch.

21. Apparatus according to claim 2 in which said heading guide support is of magnetic material and said heading guide is at least in part of a material attracted by said magnetic material.

22. Apparatus for lateral extradural lumbar disc puncture comprising an elongated index guide adapted to be secured to the back of the patient extending longitudinally relative to the lumbar vertebrae in fixed relation to the spinous processes of said vertebrae, a needle angle guide having guide means and an extension arm at an angle to said guide means, first means for securing said arm to said index guide in a plurality of positions of adjustment longitudinally and transversely, a heading guide, second means supporting said heading guide relative to said index guide, said heading guide having a radiologically visible portion and a depending portion in proximity to said guide means to assist the surgeon in directing a needle projected through said guide means into docking contact with a disc while avoiding nerve root damage.

23. Apparatus according to claim 22 in which said second means comprises, a first member extending upward from said index guide and also overlying the patient, third means adjustably positioning said first member relative to said index guide, a second member extending horizontally and longitudinally over said side of the patient, and fourth means adjustably positioning said heading guide relative to said second member.

24. Apparatus according to claim 23 in which at least a portion of said first member, said second member, and at least a portion of said heading guide are of magnetizable material and detachably secured relative to each other by magnetic attraction.

25. A method for stereotaxic extradural disc puncture comprising the steps of:

first making a radiographic image in vertical projection and determining from said image the depth from the skin surface of the intervertebral disc into which a pharmaceutical is to be injected;

second, making a radiographic image in vertical projection and determining a heading along a line viewed in vertical projection bisecting the angle between the end plates of the vertebrae to either side of said disc;

third, locating the site of skin puncture by measuring vertically from the midsaggital plane a distance calculated from the tangent of the desired angle of needle penetration and said depth in the vertical plane of said heading;

fourth, inserting a needle into the patient at said site at said angle of penetration and radiographically monitoring penetration of said needle on said heading until said disc is penetrated inward of the facet joint adjacent said disc; and injecting a pharmaceutical through said needle into said disc.

26. A method according to claim 25 in which said first step is performed by making a radiographic film in vertical projection of said disc and adjacent vertebrae with a radiopaque marker on the skin surface and a ruler with radiopaque markings supported at the midsaggital plane casting a shadow showing on said film true distances.

27. A method according to claim 26 in which said second step is performed by (a) marking a line corresponding to said heading on the film of said first step; and (b) during the performance of said second step locating a semi-radiopaque marker horizontally in line with said heading.

28. The method of claim 25 in which said third step comprises first monitoring the correct position of the patient by making a posteroanterior radiographic image and adjusting said position so that the image of the spinous process is midway between the images of the pedicles.

29. The method of claim 25 in which said third step comprises placing at least one radiopaque marker on the skin overlying the spinous process and said measuring is performed by measuring from a and axial line through said marker.

30. The method of claim 25 in which the distal end of said puncturing needle is curved and in which said fourth step is performed while radiologically monitoring said disc and turning said puncturing needle to penetrate said disc and terminate vicinal the nucleous pulposus of said disc.

31. A method according to claim 25 in which said first through fourth steps are performed with the patient lying on his side.

32. A method according to claim 25 in which said angle of needle penetration is at least 45°.

* * * * *